US010801076B2

(12) United States Patent
Leeman et al.

(10) Patent No.: US 10,801,076 B2
(45) Date of Patent: *Oct. 13, 2020

(54) INFLUENZA A VIRUS VARIANTS

(71) Applicant: Vertex Pharmaceuticals Incorporated, Boston, MA (US)

(72) Inventors: Joshua Robert Leeman, Winchester, MA (US); Randal Byrn, Wayland, MA (US); Hamilton Barlow Bennett, Malden, MA (US); Douglas John Bartels, North Liberty, IA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 299 days.

This patent is subject to a terminal disclaimer.

(21) Appl. No.: 15/475,237

(22) Filed: Mar. 31, 2017

(65) Prior Publication Data

US 2017/0204478 A1    Jul. 20, 2017

Related U.S. Application Data

(63) Continuation of application No. PCT/US2015/053385, filed on Oct. 1, 2015.

(60) Provisional application No. 62/058,961, filed on Oct. 2, 2014.

(51) Int. Cl.
| | |
|---|---|
| *C12Q 1/70* | (2006.01) |
| *C07K 14/005* | (2006.01) |
| *G16H 50/30* | (2018.01) |
| *C07K 16/10* | (2006.01) |
| *C07K 16/40* | (2006.01) |
| *C12N 7/00* | (2006.01) |
| *C12N 9/12* | (2006.01) |
| *C12Q 1/02* | (2006.01) |
| *G01N 33/50* | (2006.01) |

(52) U.S. Cl.
CPC ............ *C12Q 1/701* (2013.01); *C07K 14/005* (2013.01); *C07K 16/1018* (2013.01); *C07K 16/40* (2013.01); *C12N 7/00* (2013.01); *C12N 9/1241* (2013.01); *C12Q 1/025* (2013.01); *C12Y 207/07* (2013.01); *G01N 33/5008* (2013.01); *G16H 50/30* (2018.01); *C07K 2317/34* (2013.01); *C12N 2760/16121* (2013.01); *C12N 2760/16122* (2013.01); *C12Q 2600/106* (2013.01); *C12Q 2600/136* (2013.01); *C12Q 2600/158* (2013.01); *G01N 2333/11* (2013.01); *G01N 2333/91245* (2013.01); *G01N 2500/04* (2013.01); *G01N 2500/10* (2013.01); *G01N 2800/52* (2013.01); *Y02A 90/26* (2018.01)

(58) Field of Classification Search
None
See application file for complete search history.

(56) References Cited

U.S. PATENT DOCUMENTS

| | | | |
|---|---|---|---|
| 6,951,754 B2* | 10/2005 | Hoffmann | C07K 14/005 435/320.1 |
| 7,507,826 B2 | 3/2009 | Salituro et al. | |
| 8,829,007 B2 | 9/2014 | Charifson et al. | |
| 2006/0183900 A1 | 8/2006 | Huang et al. | |
| 2008/0300267 A1 | 12/2008 | Okram et al. | |
| 2017/0204479 A1 | 7/2017 | Leeman et al. | |
| 2019/0151314 A1 | 5/2019 | Charifson et al. | |

FOREIGN PATENT DOCUMENTS

| | | |
|---|---|---|
| KR | 100708593 | 4/2007 |
| WO | 2005/095400 | 10/2005 |
| WO | 2006111616 | 10/2006 |
| WO | 2009/125395 | 10/2009 |
| WO | 2016/054312 | 4/2016 |

OTHER PUBLICATIONS

Fechter et al. J Biological Chem 2003 vol. 278 pp. 20381-20388 (Year: 2003).*
International Search Report issued for PCT Application No. PCT/US2015/053393 dated Dec. 15, 2015.
Biswas, Siddhartha K. et al., "Mutational Analysis of the Conserved Motifs of Influenza A Virus Polymerase Basic Protein 1", Journal of Virology, The American Society for Microbiology, Mar. 1, 1994, pp. 1819-1826.
Gonzalez, Susana et al., "Characterization of Influenza Virus PB1 Protein Binding to Viral RNA: Two Separate Regions of the Protein Contribute to the Interaction Domain", Journal of Virology, The American Society for Microbiology, vol. 73, No. 1, Jan. 1, 1999, pp. 631-637.
International Search Report issued for PCT Application No. PCT/US2015/053385 dated Dec. 17, 2015.
Nakazawa, Misako et al., "PA subunit of RNA polymerase as a promising target for anti-influenza virus agents", Antiviral Research, Elsevier, vol. 78, No. 3, Jan. 17, 2008, pp. 194-201.
Sheu, Tiffany G. et al., "Dual Resistance to Adamantanes and Oseltamivir Among Seasonal Influenza A(H1N1) Viruses: 2008-2010", Journal of Infectious Diseases, vol. 203, No. 1, Jan. 1, 2011, pp. 13-17.
Subbarao, E. Kanta et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influenza A Virus Vaccine", Journal of Virology, The American Society for Microbiology, vol. 69, No. 10, Oct. 1, 1995, pp. 5969-5977.

(Continued)

*Primary Examiner* — Shanon A. Foley
*Assistant Examiner* — Myron G Hill
(74) *Attorney, Agent, or Firm* — Honigman LLP; Andrew N. Weber; Jonathan P. O'Brien

(57) ABSTRACT

The present invention relates to influenza A virus variants, particularly variants that are resistant to a polymerase inhibitors. Also provided are methods and compositions related to the influenza A virus variants. Further provided are methods of isolating, identifying, and characterizing multiple viral variants from a patient.

14 Claims, No Drawings

Specification includes a Sequence Listing.

(56) References Cited

OTHER PUBLICATIONS

CDC Seasonal Influenza, "How the Flu Virus Can Change: "Drift" and "Shift"", Centers for Disease Control and Prevention, 2011, Whole Document.
Clark, Michael P. et al., "Discovery of a Novel, First-in-Class, Orally Bioavailable Azaindole Inhibitor (VX-787) of Influenza PB2", Journal of Medicinal Chemistry, vol. 57, No. 15, Jul. 14, 2014, pp. 6668-6678.
Naito, Tadasuke et al., "Function of Influenza virus RNA polymerase on the structural basis", Virus, vol. 59, 2009, pp. 1-12.

* cited by examiner

SEQUENCE LISTING

```
<160> NUMBER OF SEQ ID NOS: 8

<210> SEQ ID NO 1
<211> LENGTH: 759
<212> TYPE: PRT
<213> ORGANISM: Influenza A virus

<400> SEQUENCE: 1

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80
```

```
Met Asn Asp Ala Gly Ser Asp Arg Val Met Val Ser Pro Leu Ala Val
                 85                  90                  95

Thr Trp Trp Asn Arg Asn Gly Pro Ile Thr Asn Thr Val His Tyr Pro
            100                 105                 110

Lys Ile Tyr Lys Thr Tyr Phe Glu Arg Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
            275                 280                 285

Ile Gly Gly Ile Arg Met Val Asp Ile Leu Arg Gln Asn Pro Thr Glu
        290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Val Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Val Glu Pro Ile Asp Asn Val Met Gly Met Ile Gly Ile Leu
    450                 455                 460

Pro Asp Met Thr Pro Ser Ile Glu Met Ser Met Arg Gly Val Arg Ile
465                 470                 475                 480

Ser Lys Met Gly Val Asp Glu Tyr Ser Ser Thr Glu Arg Val Val Val
                485                 490                 495
```

```
Ser Ile Asp Arg Phe Leu Arg Ile Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Ile
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 2
<211> LENGTH: 12
<212> TYPE: DNA
<213> ORGANISM: Artificial Sequence
<220> FEATURE:
<223> OTHER INFORMATION: Sub-Synthetic Oligonucleotide

<400> SEQUENCE: 2
agcraaagca gg                                                         12

<210> SEQ ID NO 3
<211> LENGTH: 36
<212> TYPE: DNA
<213> ORGANISM: Artificial Sequence
<220> FEATURE:
<223> OTHER INFORMATION: Sub-Synthetic Oligonucleotide
<220> FEATURE:
<221> NAME/KEY: misc_feature
<222> LOCATION: (7)..(7)
<223> OTHER INFORMATION: n is a, c, g, t or u

<400> SEQUENCE: 3 cgtctcngggg agcgaaagca ggtactgatc caaaat                              36
```

```
<210> SEQ ID NO 4
<211> LENGTH: 36
<212> TYPE: DNA
<213> ORGANISM: Artificial Sequence
<220> FEATURE:
<223> OTHER INFORMATION: Sub-Synthetic Oligonucleotide
<220> FEATURE:
<221> NAME/KEY: misc_feature
<222> LOCATION: (7)..(7)
<223> OTHER INFORMATION: n is a, c, g, t or u

<400> SEQUENCE: 4
cgtctcntat tagtagaaac aaggtacttt tttgga                              36

<210> SEQ ID NO 5
<211> LENGTH: 35
<212> TYPE: DNA
<213> ORGANISM: Artificial Sequence
<220> FEATURE:
<223> OTHER INFORMATION: Sub-Synthetic Oligonucleotide
<220> FEATURE:
<221> NAME/KEY: misc_feature
<222> LOCATION: (7)..(7)
<223> OTHER INFORMATION: n is a, c, g, t or u

<400> SEQUENCE: 5
cgtctcnggg agcgaaagca ggcaaaccat ttgaa                               35

<210> SEQ ID NO 6
<211> LENGTH: 36
<212> TYPE: DNA
<213> ORGANISM: Artificial Sequence
<220> FEATURE:
<223> OTHER INFORMATION: Sub-Synthetic Oligonucleotide
<220> FEATURE:
<221> NAME/KEY: misc_feature
<222> LOCATION: (7)..(7)
<223> OTHER INFORMATION: n is a, c, g, t or u

<400> SEQUENCE: 6
cgtctcntat tagtaggaac aaggcatttt ttcatg                              36

<210> SEQ ID NO 7
<211> LENGTH: 36
<212> TYPE: DNA
<213> ORGANISM: Artificial Sequence
<220> FEATURE:
<223> OTHER INFORMATION: Sub-Synthetic Oligonucleotide
<220> FEATURE:
<221> NAME/KEY: misc_feature
<222> LOCATION: (7)..(7)
<223> OTHER INFORMATION: n is a, c, g, t or u

<400> SEQUENCE: 7
cgtctcnggg agcgaaagca ggtcaattat attcaa                              36

<210> SEQ ID NO 8
<211> LENGTH: 36
<212> TYPE: DNA
<213> ORGANISM: Artificial Sequence
<220> FEATURE:
<223> OTHER INFORMATION: Sub-Synthetic Oligonucleotide
<220> FEATURE:
<221> NAME/KEY: misc_feature
<222> LOCATION: (7)..(7)
<223> OTHER INFORMATION: n is a, c, g, t or u
```

```
<400> SEQUENCE: 8
cgtctcntat tagtagaaac aaggtcgttt ttaaac                                    36
```

INFLUENZA A VIRUS VARIANTS

CROSS REFERENCE TO RELATED APPLICATION

This patent application is a continuation of PCT application no. PCT/US2015/053385, filed on Oct. 1, 2015, which claims priority to U.S. provisional application Ser. No. 62/058,961, filed on Oct. 2, 2014. Each of these documents is hereby incorporated by reference in its entirety.

SEQUENCE LISTING

This application incorporates by reference in its entirety the Sequence Listing entitled "355615_ST25.txt" (8.40 kilobytes), which was created on Oct. 2, 2014 and filed electronically herewith.

BACKGROUND OF THE INVENTION

Influenza spreads around the world in seasonal epidemics, resulting in the deaths of hundreds of thousands annually—millions in pandemic years. For example, three influenza pandemics occurred in the 20th century and killed tens of millions of people, with each of these pandemics being caused by the appearance of a new strain of the virus in humans. Often, these new strains result from the spread of an existing influenza virus to humans from other animal species.

Influenza is primarily transmitted from person to person via large virus-laden droplets that are generated when infected persons cough or sneeze; these large droplets can then settle on the mucosal surfaces of the upper respiratory tracts of susceptible individuals who are near (e.g. within about 6 feet) infected persons. Transmission might also occur through direct contact or indirect contact with respiratory secretions, such as touching surfaces contaminated with influenza virus and then touching the eyes, nose or mouth. Adults might be able to spread influenza to others from 1 day before getting symptoms to approximately 5 days after symptoms start. Young children and persons with weakened immune systems might be infectious for 10 or more days after onset of symptoms.

Influenza viruses are RNA viruses of the family Orthomyxoviridae, which comprises five genera: Influenza virus A, Influenza virus B, Influenza virus C, Isavirus and Thogoto virus.

The Influenza virus A genus has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to these viruses. The serotypes that have been confirmed in humans, ordered by the number of known human pandemic deaths, are: H1N1 (which caused Spanish influenza in 1918), H2N2 (which caused Asian Influenza in 1957), H3N2 (which caused Hong Kong Flu in 1968), H5N1 (a pandemic threat in the 2007-08 influenza season), H7N7 (which has unusual zoonotic potential), H1N2 (endemic in humans and pigs), H9N2, H7N2, H7N3 and H10N7.

The Influenza virus B genus has one species, influenza B virus. Influenza B almost exclusively infects humans and is less common than influenza A. The only other animal known to be susceptible to influenza B infection is the seal. This type of influenza mutates at a rate 2-3 times slower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

The Influenza virus C genus has one species, influenza C virus, which infects humans and pigs and can cause severe illness and local epidemics. However, influenza C is less common than the other types and usually seems to cause mild disease in children.

Influenza A, B and C viruses are very similar in structure. The virus particle is 80-120 nanometers in diameter and usually roughly spherical, although filamentous forms can occur. Unusually for a virus, its genome is not a single piece of nucleic acid; instead, it contains seven or eight pieces of segmented negative-sense RNA. The Influenza A genome encodes 11 proteins: hemagglutinin (HA), neuraminidase (NA), nucleoprotein (NP), M1, M2, NS1, NS2(NEP), PA, PB1, PB1-F2 and PB2.

HA and NA are large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins have been targets for antiviral drugs. Furthermore, they are antigens to which antibodies can be raised. Influenza A viruses are classified into subtypes based on antibody responses to HA and NA, forming the basis of the H and N distinctions (vide supra) in, for example, H5N1.

Influenza produces direct costs due to lost productivity and associated medical treatment, as well as indirect costs of preventative measures. In the United States, influenza is responsible for a total cost of over $10 billion per year, while it has been estimated that a future pandemic could cause hundreds of billions of dollars in direct and indirect costs. Preventative costs are also high. Governments worldwide have spent billions of U.S. dollars preparing and planning for a potential H5N1 avian influenza pandemic, with costs associated with purchasing drugs and vaccines as well as developing disaster drills and strategies for improved border controls.

Current treatment options for influenza include vaccination, and chemotherapy or chemoprophylaxis with anti-viral medications. Vaccination against influenza with an influenza vaccine is often recommended for high-risk groups, such as children and the elderly, or in people that have asthma, diabetes, or heart disease. However, it is possible to get vaccinated and still get influenza. The vaccine is reformulated each season for a few specific influenza strains but cannot possibly include all the strains actively infecting people in the world for that season. It takes about six months for the manufacturers to formulate and produce the millions of doses required to deal with the seasonal epidemics; occasionally, a new or overlooked strain becomes prominent during that time and infects people although they have been vaccinated (as by the H3N2 Fujian flu in the 2003-2004 influenza season). It is also possible to get infected just before vaccination and get sick with the very strain that the vaccine is supposed to prevent, as the vaccine takes about two weeks to become effective.

Further, the effectiveness of these influenza vaccines is variable. Due to the high mutation rate of the virus, a particular influenza vaccine usually confers protection for no more than a few years. A vaccine formulated for one year may be ineffective in the following year, since the influenza virus changes rapidly over time, and different strains become dominant.

Also, because of the absence of RNA proofreading enzymes, the RNA-dependent RNA polymerase of influenza vRNA makes a single nucleotide insertion error roughly every 10 thousand nucleotides, which is the approximate length of the influenza vRNA. Hence, nearly every newly-manufactured influenza virus is a mutant—antigenic drift. The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

Antiviral drugs can also be used to treat influenza, with neuraminidase inhibitors being particularly effective, but viruses can develop resistance to the standard antiviral drugs.

Thus, there is still a need for drugs for treating influenza infections, such as for drugs with expanded treatment window, and/or reduced sensitivity to viral titer.

Accordingly, there exists a need in identifying mutated influenza A viruses or other viruses that exhibit resistance to drugs or other therapies and in developing new viral therapeutics effective against these mutated viruses.

SUMMARY OF THE INVENTION

Accordingly, the present invention provides influenza A virus variants, and related methods and compositions. In particular, influenza A virus variants and variant influenza A virus polymerases that have reduced sensitivity to one or more polymerase inhibitors are provided.

In one aspect, this invention provides an isolated influenza A virus polynucleotide, a biologically active analog thereof, or a biologically active fragment thereof, comprising a mutation in the gene encoding the influenza A virus polymerase wherein said mutation results in at least one amino acid substitution corresponding to amino acid residues selected from the group consisting of amino acid 306, 323, 324, 337, 363, 376, 404, 431, and 510 of a wild-type influenza A virus.

In certain embodiments, the isolated influenza A virus polynucleotide comprises a nucleotide corresponding to amino acid 306 of the wild-type influenza A virus polynucleotide that does not encode Q. In certain embodiments, the nucleotide encodes H or L.

In certain embodiments, the isolated influenza A virus polynucleotide comprises a nucleotide corresponding to amino acid 323 of the wild-type influenza A virus polynucleotide that does not encode F. In certain embodiments, the nucleotide encodes S or Y.

In certain embodiments, the isolated influenza A virus polynucleotide comprises a nucleotide corresponding to amino acid 324 of the wild-type influenza A virus polynucleotide that does not encode S. In certain embodiments, the nucleotide encodes G, I, N or R.

In certain embodiments, the isolated influenza A virus polynucleotide comprises a nucleotide corresponding to amino acid 337 of the wild-type influenza A virus polynucleotide that does not encode S. In certain embodiments, the nucleotide encodes L or P.

In certain embodiments, the isolated influenza A virus polynucleotide comprises a nucleotide corresponding to amino acid 363 of the wild-type influenza A virus polynucleotide that does not encode F. In certain embodiments, the nucleotide encodes L.

In certain embodiments, the isolated influenza A virus polynucleotide comprises a nucleotide corresponding to amino acid 376 of the wild-type influenza A virus polynucleotide that does not encode K. In certain embodiments, the nucleotide encodes N, Q or R.

In certain embodiments, the isolated influenza A virus polynucleotide comprises a nucleotide corresponding to amino acid 404 of the wild-type influenza A virus polynucleotide that does not encode F. In certain embodiments, the nucleotide encodes Y.

In certain embodiments, the isolated influenza A virus polynucleotide comprises a nucleotide corresponding to amino acid 431 of the wild-type influenza A virus polynucleotide that does not encode M. In certain embodiments, the nucleotide encodes I or T.

In certain embodiments, the isolated influenza A virus polynucleotide comprises a nucleotide corresponding to amino acid 510 of the wild-type influenza A virus polynucleotide that does not encode N. In certain embodiments, the nucleotide encodes K or T.

In certain embodiments, the nucleotides that correspond to any 2 amino acids selected from the group consisting of amino acids 306, 323, 324, 337, 363, 376, 404, 431, and 510 are mutated such that the nucleotides encode an amino acid different from the amino acid encoded by the corresponding wild-type influenza A virus polynucleotide. In certain embodiments, the nucleotides that correspond to any 3 amino acids selected from the group consisting of amino acids 306, 323, 324, 337, 363, 376, 404, 431, and 510 are mutated such that the nucleotides encode an amino acid different from the amino acid encoded by the corresponding wild-type influenza A virus polynucleotide.

In further embodiments, this invention provides methods and compositions involving an influenza A virus of the invention. For example, an expression system comprising the influenza A virus is provided, and such expression system may include a vector that comprises the influenza A virus operably linked to a promoter; also provided is a host cell transfected, transformed, or transduced with the vector. Alternatively, an expression system of the invention is based on an mRNA display technology, e.g., the RNA-protein fusion technology as described in U.S. Pat. No. 6,258,558 or the in vitro "virus" technology as described in U.S. Pat. No. 6,361,943.

In another aspect, this invention provides an isolated influenza A virus variant comprising a polynucleotide encoding an influenza A virus polymerase, wherein at least one amino acid at at least one position selected from the group consisting of 306, 323, 324, 337, 363, 376, 404, 431, and 510 is mutated such that it encodes an amino acid different from the corresponding amino acid of the wild-type influenza A virus polynucleotide. Further embodiments of the invention provide methods and compositions involving the influenza A virus variants. For example, a method is provided to identify a compound that can inhibit replication of an influenza A virus variant of the invention; a cell is provided that is infected by an influenza A virus variant of the invention.

In another aspect, this invention provides an isolated influenza A virus polymerase comprising an amino acid sequence in which the amino acid at at least one position selected from the group consisting of 306, 323, 324, 337, 363, 376, 404, 431, and 510 is different from the amino acid at the corresponding position of the wild-type influenza A virus polymerase. In some embodiments, the influenza A virus polymerase comprises a biologically active analog of an influenza A virus polymerase. In some embodiments, the influenza A virus polymerase comprises a biologically active fragment of an influenza A virus polymerase.

In a further aspect, this invention provides an anti-influenza A virus polymerase antibody that recognizes an influenza A virus polymerase comprising an amino acid sequence in which the amino acid at at least one position selected from the group consisting of 306, 323, 324, 337, 363, 376, 404, 431, and 510 is different from the amino acid at the corresponding position of the wild-type influenza A virus polymerase. Further embodiments of the invention provide methods and compositions involving an anti-influenza A virus polymerase antibody of the invention. For example, a diagnostic kit comprising an antibody of the invention, and a pharmaceutical composition comprising an antibody of the invention and a pharmaceutically acceptable carrier are provided.

In another aspect, this invention provides a nucleotide probe or primer capable of hybridizing under stringent conditions to a nucleic acid sequence of an influenza A virus polynucleotide of the invention. Further embodiments of the invention provide methods and compositions involving the probe or primer. For example, a diagnostic or detection kit comprising a probe or primer of the invention is provided, and the kit is useful in, e.g., determining whether an influenza A virus variant or an influenza A virus polymerase of the invention is present in a sample.

In a further aspect, this invention provides a method for evaluating drug resistance or sensitivity to a polymerase inhibitor of an influenza A virus infection in a patient comprising: a) collecting a biological sample from the influenza A virus infected patient; and b) evaluating whether the sample comprises a nucleic acid encoding an influenza A virus polymerase that comprises an amino acid sequence in which the amino acid at at least one position selected from the group consisting of 306, 323, 324, 337, 363, 376, 404, 431, and 510 is different from the amino acid at each corresponding position of the wild-type influenza A virus polymerase.

Also provided is a method for guiding a treatment for an influenza A virus infection in a patient comprising: a) evaluating drug resistance or sensitivity to a polymerase inhibitor of the patient according the method of claim 23; and b) optimizing the treatment regimen for the patient based on the drug resistance or sensitivity evaluated in a). For example, if drug resistance is predicted or detected (e.g., reduced sensitivity to a polymerase inhibitor), one or more other compounds or agents may be included in the patient's treatment plan or therapeutic regimen. The method may comprise any combination of determining the sequence (e.g., genotyping) of an influenza A virus polymerase in the patient, determining the sensitivity to a polymerase inhibitor (e.g., phenotyping), or determining the viral fitness level of the patient's influenza A virus. The phenotyping may be carried out in a cell-free system (e.g., in vitro protease assays) as well as a cell-based system (e.g., replicon assays or viral infection or replication assays).

In another aspect, this invention provides a method for identifying a candidate compound for treating an influenza A virus infection in a patient comprising: a) providing a sample infected with the influenza A virus variant; and b) assaying the ability of the candidate compound in inhibiting an activity of the influenza A virus variant in the sample. The sample may be obtained from a patient's cells or plasma. The sample infected with an influenza A virus variant may also be cultured cells. The activity of the influenza A virus variant may be determined by its ability to infect, replicate, and/or become released.

Alternatively, such a method may comprise providing a replicon RNA comprising an influenza A virus polynucleotide of the invention and determining whether the candidate compound inhibits replication of the replicon RNA in a suitable assay.

Another alternative method may comprise providing an isolated influenza A virus polymerase of invention and a polymerase substrate, and determining whether the influenza A virus polymerase activity is reduced in the presence of a candidate compound; the influenza A virus polymerase and/or the polymerase substrate may be in a cell-based system, for example expressed in cultured cells, or the influenza A virus polymerase and/or the polymerase substrate may be in a cell-free system, for example a reaction mixture including an influenza A virus polymerase and a peptide substrate.

A further alternative method for evaluating a candidate compound for treating an influenza A virus infection in a patient may include introducing a vector comprising an influenza A virus polynucleotide of the invention and an indicator gene encoding an indicator into a host cell and measuring the indicator in the presence of the candidate compound and in the absence of the candidate compound.

A further aspect of this invention provides a method for treating an influenza A virus infection in a patient. The method may comprise administering to the patient a pharmaceutically or therapeutically effective amount of a compound identified by a method of the invention alone or in combination with another anti-viral agent.

Another aspect of the invention relates to computer tools, which provides a machine-readable data storage medium comprising a data storage material encoded with machine-readable data, wherein the machine-readable data comprise index values for at least two features associated with an influenza A virus variant or biological sample.

The features are selected from: a) the ability to exhibit resistance for reduced sensitivity to a polymerase inhibitor; b) an influenza A virus polymerase comprising an amino acid sequence in which the amino acid at at least one position selected from the group consisting of: 306, 323, 324, 337, 363, 376, 404, 431, and 510 of a wild-type influenza A virus is different from the amino acid at the corresponding position of the wild-type influenza A virus polymerase; c) morbidity or recovery potential of a patient; and d) altered replication capacity (increased or decreased) of the influenza A virus variant.

A further aspect of the invention provides a method of obtaining a profile of influenza A virus variants in an influenza A virus-infected patient. The method may comprise obtaining a sample (e.g., a plasma sample) from the patient and genotyping and/or phenotyping an influenza A virus polymerase from at least 2, 20, 50, 100, 200, 500 or more influenza A virus virions from the sample. For example, such genotyping may include determining the nucleotide sequence of an influenza A virus polymerase from at least 2, 20, 50, 100, 200, 500 or more influenza A virus virions from the plasma sample.

In certain embodiments, the patient subjected to such profiling may have been treated or be selected to be treated with a polymerase inhibitor.

In certain embodiments, plasma samples are obtained from the patient subjected to such profiling at two or more different time points.

DETAILED DESCRIPTION OF THE INVENTION

The present invention relates to influenza A virus variants. In particular, influenza A virus variants that exhibit resistance to a polymerase inhibitor are provided. Also provided are methods and compositions related to the influenza A virus variants. The methods and compositions are useful in identifying viral variants, including variants of an influenza A virus and other viruses, evaluating and identifying antiviral compounds, and developing and optimizing therapeutics against viral infections.

Influenza A Virus Variants and Related Polynucleotides and Polymerases

The present invention provides influenza A virus variants. In particular embodiments, an influenza A virus variant includes a polynucleotide sequence that encodes an influenza A virus polymerase with reduced sensitivity to a polymerase inhibitor (also termed "a variant influenza A virus polymerase"), such as Compound 1. As used herein, a wild-type influenza A virus refers to an influenza A virus comprising a polynucleotide (also termed "a wild-type polynucleotide") that encodes an influenza A virus polymerase with normal or desirable sensitivity to a polymerase inhibitor, and in particular embodiments, the polymerase inhibitor is Compound 1. Similarly, a wild-type influenza A virus polymerase refers to an influenza A virus polymerase with normal or desirable sensitivity to a polymerase inhibitor, and in particular embodiments, the polymerase inhibitor is Compound 1.

In some embodiments, the wild-type influenza A virus comprises the amino acid sequence of SEQ ID NO: 1. In some embodiments, the wild-type influenza A virus comprises an amino acid sequence having at least 70, 75, 80, 85, 90, 95, 97 or 99% homology to SEQ ID NO: 1.

The terms "influenza virus mediated condition", "influenza infection", "Influenza", or "flu" as used herein, are used interchangeable to mean the disease caused by an infection with an influenza virus.

Influenza is an infectious disease that affects birds and mammals caused by influenza viruses. Influenza viruses are RNA viruses of the family Orthomyxoviridae, which comprises five genera: *Influenzavirus A, Influenzavirus B, Influenzavirus C, Isavirus* and *Thogotovirus*. *Influenzavirus A* genus has one species, influenza A virus which can be subdivided into different serotypes based on the antibody response to these viruses: H1N1, H2N2, H3N2, H5N1, H7N7, H1N2, H9N2, H7N2, H7N3 and H10N7. *Influenzavirus B* genus has one species, influenza B virus. Influenza B almost exclusively infects humans and is less common than influenza A. *Influenzavirus C* genus has one species, *Influenzavirus C* virus, which infects humans and pigs and can cause severe illness and local epidemics. However, *Influenzavirus C* is less common than the other types and usually seems to cause mild disease in children.

In some embodiments of the invention, influenza or influenza viruses are associated with *Influenzavirus A* or *B*. In some embodiments of the invention, influenza or influenza viruses are associated with *Influenzavirus A*. In some specific embodiments of the invention, *Influenzavirus A* is H1N1, H2N2, H3N2 or H5N1.

In humans, common symptoms of influenza are chills, fever, pharyngitis, muscle pains, severe headache, coughing, weakness, and general discomfort. In more serious cases, influenza causes pneumonia, which can be fatal, particularly in young children and the elderly. Although it is often confused with the common cold, influenza is a much more severe disease and is caused by a different type of virus. Influenza can produce nausea and vomiting, especially in children, but these symptoms are more characteristic of the unrelated gastroenteritis, which is sometimes called "stomach flu" or "24-hour flu".

Symptoms of influenza can start quite suddenly one to two days after infection. Usually the first symptoms are chills or a chilly sensation, but fever is also common early in the infection, with body temperatures ranging from 38-39° C. (approximately 100-103° F.). Many people are so ill that they are confined to bed for several days, with aches and pains throughout their bodies, which are worse in their backs and legs. Symptoms of influenza may include: body aches, especially joints and throat, extreme coldness and fever, fatigue, Headache, irritated watering eyes, reddened eyes, skin (especially face), mouth, throat and nose, abdominal pain (in children with influenza B). Symptoms of influenza are non-specific, overlapping with many pathogens ("influenza-like illness"). Usually, laboratory data is needed in order to confirm the diagnosis.

The terms, "disease", "disorder", and "condition" may be used interchangeably here to refer to an influenza virus mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In a preferred embodiment, the subject is a "human".

The term "biological sample", as used herein, includes, without limitation, cell cultures or extracts thereof; biopsied material obtained from a mammal or extracts thereof; blood, saliva, urine, feces, semen, tears, or other body fluids or extracts thereof.

As used herein, "multiplicity of infection" or "MOI" is the ratio of infectious agents (e.g. phage or virus) to infection targets (e.g. cell). For example, when referring to a group of cells inoculated with infectious virus particles, the multiplicity of infection or MOI is the ratio defined by the number of infectious virus particles deposited in a well divided by the number of target cells present in that well.

As used herein the term "inhibition of the replication of influenza viruses" includes both the reduction in the amount of virus replication (e.g. the reduction by at least 10%) and the complete arrest of virus replication (i.e., 100% reduction in the amount of virus replication). In some embodiments, the replication of influenza viruses are inhibited by at least 50%, at least 65%, at least 75%, at least 85%, at least 90%, or at least 95%.

Influenza virus replication can be measured by any suitable method known in the art. For example, influenza viral titre in a biological sample (e.g. an infected cell culture) or in humans (e.g. lung viral titre in a patient) can be measured. More specifically, for cell based assays, in each case cells are cultured in vitro, virus is added to the culture in the presence or absence of a test agent, and after a suitable length of time a virus-dependent endpoint is evaluated. For typical assays, the Madin-Darby canine kidney cells (MDCK) and the standard tissue culture adapted influenza strain, A/Puerto Rico/8/34 can be used. A first type of cell assay that can be used in the invention depends on death of the infected target cells, a process called cytopathic effect (CPE), where virus infection causes exhaustion of the cell resources and eventual lysis of the cell. In the first type of cell assay, a low fraction of cells in the wells of a microtiter plate are infected (typically 1/10 to 1/1000), the virus is allowed to go through several rounds of replication over 48-72 hours, then the amount of cell death is measured using a decrease in cellular ATP content compared to uninfected controls. A second type of cell assay that can be employed in the invention depends on the multiplication of virus-specific RNA molecules in the infected cells, with RNA levels being directly measured using the branched-chain DNA hybridization method (bDNA). In the second type of cell assay, a low number of cells are initially infected in wells of a microtiter plate, the virus is allowed to replicate in the infected cells and spread to additional rounds of cells, then the cells are lysed and viral RNA content is measured. This assay is stopped early, usually after 18-36 hours, while all the target cells are still viable. Viral RNA is quantitated by hybridization to specific oligonucleotide probes fixed to wells of an assay plate, then amplification of the signal by hybridization with additional probes linked to a reporter enzyme.

As used herein a "viral titer" (or titre) is a measure of virus concentration. Titer testing can employ serial dilution to obtain approximate quantitative information from an analytical procedure that inherently only evaluates as positive or negative. The titer corresponds to the highest dilution factor that still yields a positive reading; for example, positive readings in the first 8 serial twofold dilutions translate into a titer of 1:256. A specific example is viral titer. To determine the titer, several dilutions will be prepared, such as 10-1, 10-2, 10-3, . . . , 10-8. The lowest concentration of virus that still infects cells is the viral titer.

As used herein, the terms "treat", "treatment", and "treating" refer to both therapeutic and prophylactic treatments. For example, therapeutic treatments includes the reduction or amelioration of the progression, severity and/or duration of influenza viruses mediated conditions, or the amelioration of one or more symptoms (specifically, one or more discernible symptoms) of influenza viruses mediated conditions, resulting from the administration of one or more therapies (e.g., one or more therapeutic agents such as a compound or composition of the invention). In specific embodiments, the therapeutic treatment includes the amelioration of at least one measurable physical parameter of an influenza virus mediated condition. In other embodiments the therapeutic treatment includes the inhibition of the progression of an influenza virus mediated condition, either physically by, e.g., stabilization of a discernible symptom, physiologically by, e.g., stabilization of a physical parameter, or both. In other embodiments the therapeutic treatment includes the reduction or stabilization of influenza viruses mediated infections. Antiviral drugs can be used in the community setting to treat people who already have influenza to reduce the severity of symptoms and reduce the number of days that they are sick.

The term "chemotherapy" refers to the use of medications, e.g. small molecule drugs (rather than "vaccines") for treating a disorder or disease.

The terms "prophylaxis" or "prophylactic use" and "prophylactic treatment" as used herein, refer to any medical or public health procedure whose purpose is to prevent, rather than treat or cure a disease. As used herein, the terms "prevent", "prevention", and "preventing" refer to the reduction in the risk of acquiring or developing a given condition, or the reduction or inhibition of the recurrence or said condition in a subject who is not ill, but who has been or may be near a person with the disease. The term "chemoprophylaxis" refers to the use of medications, e.g. small molecule drugs (rather than "vaccines") for the prevention of a disorder or disease.

As used herein, prophylactic use includes the use in situations in which an outbreak has been detected, to prevent contagion or spread of the infection in places where a lot of people that are at high risk of serious influenza complications live in close contact with each other (e.g. in a hospital ward, daycare center, prison, nursing home, etc.). It also includes the use among populations who require protection from the influenza but who either do not get protection after vaccination (e.g. due to weak immune system), or when the vaccine is unavailable to them, or when they cannot get the vaccine because of side effects. It also includes use during the two weeks following vaccination, since during that time the vaccine is still ineffective. Prophylactic use may also include treating a person who is not ill with the influenza or not considered at high risk for complications, in order to reduce the chances of getting infected with the influenza and passing it on to a high-risk person in close contact with him (for instance, healthcare workers, nursing home workers, etc.).

According to the US CDC, an influenza "outbreak" is defined as a sudden increase of acute febrile respiratory illness (AFRI) occurring within a 48 to 72 hour period, in a group of people who are in close proximity to each other (e.g. in the same area of an assisted living facility, in the same household, etc.) over the normal background rate or when any subject in the population being analyzed tests positive for influenza. One case of confirmed influenza by any testing method is considered an outbreak.

A "cluster" is defined as a group of three or more cases of AFRI occurring within a 48 to 72 hour period, in a group of people who are in close proximity to each other (e.g. in the same area of an assisted living facility, in the same household, etc.).

As used herein, the "index case", "primary case", or "patient zero" is the initial patient in the population sample of an epidemiological investigation. When used in general to refer to such patients in epidemiological investigations, the term is not capitalized. When the term is used to refer to a specific person in place of that person's name within a report on a specific investigation, the term is capitalized as Patient Zero. Often scientists search for the index case to determine how the disease spread and what reservoir holds the disease in between outbreaks. Note that the index case is the first patient that indicates the existence of an outbreak. Earlier cases may be found and are labeled primary, secondary, tertiary, etc.

In one embodiment, the methods of the invention are a preventative or "pre-emptive" measure to a patient, specifically a human, having a predisposition to complications resulting from infection by an influenza virus. The term "pre-emptive" as used herein as for example in pre-emptive use, "pre-emptively," etc., is the prophylactic use in situations in which an "index case" or an "outbreak" has been confirmed, in order to prevent the spread of infection in the rest of the community or population group.

In another embodiment, the methods of the invention are applied as a "pre-emptive" measure to members of a community or population group, specifically humans, in order to prevent the spread of infection.

As used herein, an "effective amount" refers to an amount sufficient to elicit the desired biological response. In the present invention the desired biological response is to inhibit the replication of influenza virus, to reduce the amount of influenza viruses or to reduce or ameliorate the severity, duration, progression, or onset of an influenza virus infection, prevent the advancement of an influenza viruses infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. When co-administered with other antiviral agents, e.g., when co-administered with an anti-influenza medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between approximately 0.01 to 100 mg/kg body weight/day for therapeutic or prophylactic treatment.

Generally, dosage regimens can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compounds described herein required to treat, to prevent, inhibit (fully or partially) or arrest the progress of the disease.

Dosages of the compounds described herein can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosing, such as twice a day (e.g., every 12 hours), three times a day (e.g., every 8 hours), or four times a day (e.g., every 6 hours).

For therapeutic treatment, the compounds described herein can be administered to a patient within, for example, 48 hours (or within 40 hours, or less than 2 days, or less than 1.5 days, or within 24 hours) of onset of symptoms (e.g., nasal congestion, sore throat, cough, aches, fatigue, headaches, and chills/sweats). The therapeutic treatment can last for any suitable duration, for example, for 5 days, 7 days, 10 days, 14 days, etc. For prophylactic treatment during a community outbreak, the compounds described herein can be administered to a patient within, for example, 2 days of onset of symptoms in the index case, and can be continued for any suitable duration, for example, for 7 days, 10 days, 14 days, 20 days, 28 days, 35 days, 42 days, etc.

Various types of administration methods can be employed in the invention, and are described in detail below under the section entitled "Administration Methods".

The present invention also provides isolated influenza A virus variants, isolated variant influenza A virus polymerases, and isolated polynucleotide that encodes a variant influenza A virus polymerase. The term "isolated" generally means separated and/or recovered from a component of natural environment of a subject virus, protease, or polynucleotide.

In certain embodiments, a variant influenza A virus polymerase may be a variant influenza A virus polymerase that comprises an amino acid sequence in which the amino acid(s) at one or more positions from positions 306, 323, 324, 337, 363, 376, 404, 431, and 510 of a wild-type influenza A virus polymerase is (are) different from the amino acid at each corresponding position of the wild-type influenza A virus polymerase.

Expression systems are provided, for example, to make the variant influenza A virus polymerases of the invention. An expression system may include an expression vector that comprises an influenza A virus polynucleotide of the invention. Suitable prokaryotic or eukaryotic vectors (e.g., expression vectors) comprising an influenza A virus polynucleotide (or "nucleic acid," used interchangeably herein) of the invention can be introduced into a suitable host cell by an appropriate method (e.g., transformation, transfection, electroporation, infection), such that the polynucleotide is operably linked to one or more expression control elements (e.g., in the vector or integrated into the host cell genome). For production, host cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein can be recovered and/or isolated (e.g., from the host cells or medium). It will be appreciated that the method of production encompasses expression in a host cell of a transgenic animal (see e.g., WO 92103918). An expression system may be based on a cell-free system such as the RNA-protein fusion technology described in U.S. Pat. No. 6,258,558 or the in vitro "virus" described in U.S. Pat. No. 6,361,943. Ribosome display methods can also be used, such as the method described in U.S. Pat. No. 5,843,701.

Various assays are provided, for example, assays suitable for phenotyping influenza A viruses. The assays may be directed to measuring a viral activity (e.g., infection, replication, and/or release of viral particles) or an enzymatic activity (e.g. polymerase activity). Viral activity assays may employ cells or samples infected with a virus or viral variant of which the activity is to be measured. The cells or samples may be obtained from a patient such as a human patient. Alternatively, the cells or samples may be cultured and infected with a virus or viral variant in vitro. Viral activity assays may employ a replicon-based system.

Enzymatic activity can be determined in cell-free or cell-based systems which generally include the enzyme of interest or a biologically active fragment or analog thereof and a substrate for the enzyme of interest.

In certain embodiments, the identified compound is formulated into a composition comprising the compound and a pharmaceutically acceptable carrier, adjuvant or vehicle. Preferably the composition contains the compound in an amount effective to reduce the activity of an influenza A virus polymerase. Even more preferably the composition is formulated for administration to a patient. The compositions also may comprise an additional agent selected from an immunomodulatory agent; an anti-viral agent; a second inhibitor of influenza A virus polymerase; an inhibitor of another target in the influenza A virus life cycle; or combinations thereof. The various compositions are described in greater details below.

In another aspect, the present invention provides antibodies that are specific to an influenza A virus polymerase, in particular, an influenza A virus polymerase with one or more amino acids altered as compared to a wild type influenza A virus polymerase. The term "antibody" is used in the broadest sense and specifically covers, without limitation, intact monoclonal antibodies, polyclonal antibodies, chimeric antibodies, multispecific antibodies (e.g., bispecific antibodies) formed from at least two intact antibodies, and antibody fragments, so long as they exhibit the desired biological activity. The term "immunoglobulin" includes a variety of structurally related proteins that are not necessarily antibodies.

"Antibody fragments" comprise a portion of an intact antibody, preferably the antigen-binding or variable region of the intact antibody. Examples of antibody fragments include Fab, Fab', F(ab')2, and Fv fragments; diabodies; linear antibodies; single-chain antibody molecules; and multispecific antibodies formed from antibody fragments. "Single-chain Fv" or "scFv" antibody fragments comprise the VH and VL domains of an antibody, wherein these domains are present in a single polypeptide chain. Preferably, the Fv polypeptide further comprises a polypeptide linker between the VH and VL domains that enables the scFv to form the desired structure for antigen binding.

The term "diabodies" refers to small antibody fragments with two antigen binding sites, which fragments comprise a heavy-chain variable domain (VH) connected to a light-chain variable domain (VL) in the same polypeptide chain (VHVL). By using a linker that is too short to allow pairing between the two domains on the same chain, the domains are forced to pair with the complementary domains of another chain and create two antigen-binding sites.

An antibody against a variant influenza A virus polymerase may be developed from a known antibody against an influenza A virus protein, for example through molecular evolution. Amino acid sequence variants are prepared by introducing appropriate nucleotide changes into the DNA of a known antibody, or by peptide synthesis. Such variants include, for example, deletions from, and/or insertions into and/or substitutions of, residues within the amino acid sequences of the known antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

An antibody of the invention may have diagnostic as well as therapeutic applications. In certain embodiments, an antibody of the invention is labeled. The various antibodies of the present disclosure can be used to detect or measure the expression of a variant influenza A virus polymerase, and therefore, they are also useful in applications such as cell sorting and imaging (e.g., flow cytometry, and fluorescence activated cell sorting), for diagnostic or research purposes. As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}H, ^{14}C, ^{15}N, ^{35}S, ^{90}Y, ^{99}Tc, ^{111}In, ^{125}1, ^{131}I$), fluorescent labels (e.g., FITC, rhodamine, lanthanide phosphors), enzymatic labels (e.g., horseradish peroxidase, beta-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In certain aspects, kits for use in detecting the presence of an influenza A virus, a variant influenza A virus polynucleotide, or a variant influenza A virus polymerase in a biological sample can also be prepared. Such kits may include an antibody that recognizes a variant influenza A virus polymerase of the invention, as well as one or more ancillary reagents suitable for detecting the presence of a complex between the antibody and the variant polymerase or a portion thereof. Alternatively, such kits may include a probe or primer of the invention, such a probe or primer can hybridize with a variant influenza A virus polynucleotide of the invention under stringent conditions. A probe or primer of the invention may be suitable for PCR or RT-PCR that can be employed to detect a subject of interest. Alternatively, such kits may be based on PCR or non-PCR based influenza A virus diagnostic kits available commercially.

Another aspect of the invention provides pharmaceutical compositions or formulations including a compound of the invention, for example, a secondary compound that is identified as being able to rescue the activity of a polymerase inhibitor, or a compound that is identified as effective against an influenza A virus variant (e.g., capable of reducing replication of the viral variant) and/or a variant influenza A virus polymerase (e.g., capable of reducing the enzymatic activity of the variant polymerase).

Another aspect of the invention provides uses of a compound of the invention in the manufacture of a medicament, such as a medicament for treating an influenza A virus infection in a patient.

Another aspect of the invention provides methods for treating an influenza A virus infection in a patient. Such methods generally comprise administering to the patient a pharmaceutically or therapeutically effective amount of a compound of the invention alone or in combination (sequentially or contemporaneously) with another anti-viral agent. "Effective amount" of a compound or agent generally refers to those amounts effective to reproducibly reduce influenza A virus polymerase expression or activity, influenza A virus production, replication, or virulence, influenza A virus infection, or produce an amelioration or alleviation of one or more of the symptoms of influenza A virus infection in comparison to the levels of these parameters in the absence of such a compound or agent.

In another aspect, the methods and compositions of this invention include a polymerase inhibitor and another antiviral agent, preferably an anti-influenza A virus agent. Combination therapy targeting influenza A virus is also described in WO 2010/148197.

As used herein, the terms "in combination" or "coadministration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) can permit the use of lower dosages of one or more of the therapies and/or less frequent administration of said therapies to a subject. The ability to utilize lower dosages of a therapy (e.g., a prophylactic or therapeutic agent) and/or to administer said therapy less frequently can reduce the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

Specific examples that can be co-administered with a compound described herein include neuraminidase inhibitors, such as oseltamivir (Tamiflu®) and Zanamivir (Rlenza®), viral ion channel (M2 protein) blockers, such as amantadine (Symmetrel®) and rimantadine (Flumadine®), and antiviral drugs described in WO 2003/015798, including T-705 under development by Toyama Chemical of Japan. (See also Ruruta et al., Antiviral Research, 82: 95-102 (2009), "T-705 (flavipiravir) and related compounds: Novel broad-spectrum inhibitors of RNA viral infections"). In some embodiments, the compounds described herein can be co-administered with a traditional influenza vaccine.

Nothing herein limits the methods or combinations of this invention to any specific dosage forms or regime. Thus, each component of a combination according to this invention may be administered separately, together, sequentially or simultaneously, or in any combination thereof.

Formulations, doses, and routes of administration for the foregoing molecules are well-known in the art. Alternatively, once a compound that exhibits influenza A virus antiviral activity, particularly antiviral activity against a drug-resistant strain of influenza A virus, has been identified, a pharmaceutically effective amount of that compound can be determined using techniques that are well-known to the skilled artisan. Thus, the appropriate formulations, dose(s) range, and dosing regimens, of such a compound can be easily determined by routine methods.

The compositions related to combination therapies of the present invention can be provided to a cell or cells, or to a human patient, either in separate pharmaceutically acceptable formulations administered simultaneously or sequentially, formulations containing more than one therapeutic agent, or by an assortment of single agent and multiple agent formulations. Regardless of the route of administration, these drug combinations form an anti-influenza A virus effective amount of components of the pharmaceutically acceptable formulations.

In the event of enhanced influenza A virus antiviral effectiveness of the present influenza A virus polymerase inhibitors in the presence of immunomodulators and immunostimulants, reduced amounts of these influenza A virus polymerase inhibitors can be employed in the methods and compositions contemplated herein. Such reduced amounts can be determined by routine monitoring of influenza A virus titers in infected patients undergoing therapy. This can be carried out by, for example, monitoring influenza A virus RNA in patients' serum by slot-blot, dot-blot, or RT-PCR techniques, or by measurement of influenza A virus surface or other antigens. Patients can be similarly monitored during combination therapy employing the influenza A virus polymerase inhibitors disclosed herein and other compounds having anti-influenza A virus activity to determine the lowest effective doses of each when used in combination.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional antiviral agent in the composition.

According to another embodiment, the invention provides a method for treating a patient infected with or preventing infection by a virus characterized by a virally encoded influenza polymerase that is necessary for the life cycle of the virus by administering to said patient a pharmaceutically acceptable composition of this invention. Preferably, the methods of this invention are used to treat a patient suffering from an influenza A virus infection. Such treatment may completely eradicate the viral infection or reduce the severity thereof.

In another embodiment, the compounds of this invention may be used as laboratory tools to aid in the isolation of a virally encoded influenza A virus polymerase. This method comprises the steps of providing a compound of this invention attached to a solid support; contacting said solid support with a sample containing an influenza A virus polymerase under conditions that cause said polymerase to bind to said solid support; and eluting said influenza A virus polymerase from said solid support. Preferably, the viral polymerase isolated by this method is PB2 polymerase. More particularly, it is a mutant PB2 polymerase that is resistant to treatment by polymerase inhibitors. Exemplary such polymerase includes those described herein as having mutant (i.e., non-wild-type) residues at positions 306, 323, 324, 337, 363, 376, 404, 431, and/or 510.

Compounds of the Invention

In some embodiments, the influenza A virus polymerase inhibitor is Compound 1, or a pharmaceutically acceptable salt thereof for any of the uses specified above.

Compound 1

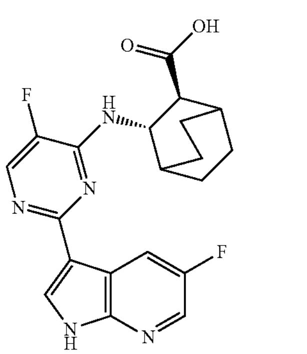

In yet another embodiment, the compounds described herein or pharmaceutically acceptable salts thereof can be used to reduce viral titre in a biological sample (e.g. an infected cell culture) or in humans (e.g. lung viral titre in a patient).

Pharmaceutically Acceptable Salts, Solvates, Chlatrates, Prodrugs and Other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and N+(C1-4alkyl)4 salts. This invention also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N, N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like.

Other acids and bases, while not in themselves pharmaceutically acceptable, may be employed in the preparation of salts useful as intermediates in obtaining the compounds described herein and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

In addition to the compounds described herein, pharmaceutically acceptable solvates (e.g., hydrates) and clathrates of these compounds may also be employed in compositions to treat or prevent the herein identified disorders.

As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders.

A "pharmaceutically acceptable derivative or prodrug" includes any pharmaceutically acceptable ester, salt of an ester or other derivative or salt thereof of a compound described herein which, upon administration to a recipient, is capable of providing, either directly or indirectly, a compound described herein or an inhibitorily active metabolite or residue thereof. Particularly favored derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —$NO^2$, —ONO, or —$ONO^2$ moieties. Prodrugs can typically be prepared using well-known methods, such as those described by Burger's Medicinal Chemistry and Drug Discovery (1995) 172-178, 949-982 (Manfred E. Wolff ed., 5th ed).

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

Pharmaceutically acceptable prodrugs of the compounds described herein include, without limitation, esters, amino acid esters, phosphate esters, metal salts and sulfonate esters.

Pharmaceutical Compositions

The compounds described herein can be formulated into pharmaceutical compositions that further comprise a pharmaceutically acceptable carrier, diluent, adjuvant or vehicle. In one embodiment, the present invention relates to a pharmaceutical composition comprising a compound of the invention described above, and a pharmaceutically acceptable carrier, diluent, adjuvant or vehicle. In one embodiment, the present invention is a pharmaceutical composition comprising an effective amount of a compound of the present invention or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

An "effective amount" includes a "therapeutically effective amount" and a "prophylactically effective amount". The term "therapeutically effective amount" refers to an amount effective in treating and/or ameliorating an influenza virus infection in a patient infected with influenza. The term "prophylactically effective amount" refers to an amount effective in preventing and/or substantially lessening the chances or the size of influenza virus infection outbreak. Specific examples of effective amounts are described above in the section entitled Uses of Disclosed Compounds.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, its use is contemplated to be within the scope of this invention. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

Some examples of materials which can serve as pharmaceutically acceptable carriers include, but are not limited to, ion exchangers, alumina, aluminum stearate, lecithin, serum proteins (such as human serum albumin), buffer substances (such as tween 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Administration Methods

The compounds and pharmaceutically acceptable compositions described above can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

Exemplification

The disclosure now being generally described, it will be more readily understood by reference to the following examples, which are included merely for purposes of illustration of certain aspects and embodiments of the present disclosure, and are not intended to limit the disclosure.

EXAMPLES

Example 1

Identification of Influenza A Virus Variants

In vitro selection experiments were performed on the influenza A/Wisconsin/67/2005 (H3N2) strain. Antiviral activity of Compound 1 was measured using MDCK cells in a three day cytopathic effect (CPE)-based assay. Variants with reduced sensitivity to Compound 1 were selected in vitro by infecting replicate wells containing MDCK cells with influenza virus at an MOI of 1.0, and monitoring the development of CPE as a surrogate for viral replication. Selection experiments were performed in 384-well plates using 32 replicate wells at each of eight concentrations of Compound 1, ranging from 1× to 128× the $EC_{50}$. Virus was sampled from the supernatant and passaged to new cells. Supernatants from wells showing virus growth in the presence of inhibitor were used to grow small virus stocks, which were characterized for Compound 1 sensitivity. For viruses showing reduced sensitivity to Compound 1, viral RNA was extracted, reverse transcribed, and PCR-amplified, followed by Sanger-based population sequencing of the PA, PB1 and PB2 coding regions. Confirmation of the effect of the primary amino acid changes on virus sensitivity to Compound 1 and virus replication capacity was performed using the reverse genetics system, and natural frequency of the identified variants was analyzed.

Variants with reduced sensitivity to Compound 1 were isolated at amino acid positions 306, 323, 324, 363, 376, 431, and 510 of the influenza A PB2 protein. These variants were found at very low frequencies (i.e., <0.01%) in the public sequence database of naturally occurring human influenza sequences. Additionally, all Compound 1-selected PB2 variants show replicative impairment as compared to wild-type virus in vitro. Variants isolated from the three resistance selection experiments are located in the cap-binding pocket of PB2 and are likely directly or indirectly altering the binding of Compound 1. These results support the mechanism of action of Compound 1 as an inhibitor of the essential 'cap-snatching' activity of the influenza polymerase complex.

Variants with reduced susceptibility to Compound 1 showed specific changes in the influenza virus PB2 gene, not in the PB1 or PA genes. Variants at PB2 amino acid positions Q306, F323, S324, F363, K376, M431, and N510 showed a greater than 10-fold shift in sensitivity to Compound 1. Reverse genetics-generated viruses containing these PB2 alterations confirmed the reduced sensitivity to Compound 1.

Most of the selected variants with reduced susceptibility to Compound 1 (S324, S337, F363, K376, F404, and M431) are located within the PB2 cap-binding region. The others, Q306H and N510T, are located in PB2 regions for which structural information is not available.

These variant positions show significant overlap with those identified in Compound 1 resistance selection experiments performed with A/Puerto Rico/8/34 and A/California/07/2009.

Example 2

Compounds, Growth Media and Media Supplements

Compound 1 was synthesized at Vertex Pharmaceuticals Incorporated and was dissolved in 100% dimethyl sulfoxide (DMSO) at a concentration of 10 mM and stored at −20° C. DMEM (catalog number 11960), 200 mM L-glutamine (catalog number 25030-081), penicillin-streptomycin liquid (catalog number 15140-122) and HEPES buffer (catalog number 15630) were purchased from Invitrogen (Carlsbad, Calif., USA). Fetal bovine serum (FBS; catalog numbers F4135 or 10091-148) was purchased from Sigma-Aldrich (St Louis, Mo., USA), or Invitrogen, respectively. DMSO (catalog number D2650) and Ex-CELL serum-free medium (catalog number M8303) were purchased from Sigma-Aldrich. CellTiterGlo® (catalog number G7573) was purchased from Promega (Madison, Wis., USA). Tolylsulfonyl phenylalanyl chloromethyl ketone (TPCK)-treated trypsin (catalog number 22725) was purchased from USB Corporation (Affymetrix, Fremont, Calif., USA).

Example 3

Viral Stocks

To allow productive infections in a canine kidney cell line (MDCK), A/Wisconsin/67/2005 (Influenza Reagent Resource, FR-397, Manassas, Va., USA) was serially passaged 10 times in MDCK cells. This adapted virus was plaque purified (designated as A/Wisconsin/67/2005-p1) and prepared by standard methods (World Health Organization). Briefly, MDCK cells (CCL-34, ATCC) were maintained in DMEM supplemented with 2 mM L-glutamine, 1× non-essential amino acids, 100 U/mL penicillin, 100 μg/mL streptomycin (complete DMEM; cDMEM) with 10% FBS. Cells were infected at low multiplicity of infection (MOI) in cDMEM with 1 μg/mL TPCK-treated trypsin (viral growth medium; VGM) for approximately 48 h, after which the supernatant was harvested by centrifugation at 650×g for 10 min with a Beckman GS-6R centrifuge. Virus stocks were frozen and stored at −80° C. The $TCID_{50}$ (amount of infective agent that will produce pathological change in 50% of cell cultures) infectious titer was determined by testing serial dilutions of the virus stock on MDCK cells in a 4-day cytopathic effect-based assay, with the results calculated by the Karber method.

TABLE 1

Equipment.

| Item | Model | Company | Location |
|---|---|---|---|
| Centrifuge | GS-6R | Beckman Coulter | Brea, CA, USA |
| Incubator | NU-8700 | Nuaire | Plymouth, MN, USA |
| Liquid Handler | Biomek FX | Beckman Coulter | Brea, CA, USA |
| Luminometer | EnVision 2103 Multilabel Plate Reader | PerkinElmer | Waltham, MA, USA |
| Spectrophotometer | NanoDrop, 8000 v.1.1 | Thermo Fisher Scientific | Waltham, MA, USA |

TABLE 2

Software.

| Purpose | Software | Company | Location |
|---|---|---|---|
| CPE Assay | Condoseo | Genedata | Basel, Switzerland |
| Data Storage and $TCID_{50}$ | Excel | Microsoft | Redmond, WA, USA |
| Protein modeling | PyMOL Molecular Graphics System 1.4.1 | Schrodinger, LLC | New York, NY, USA |
| Reporting | Word | Microsoft | Redmond, WA, USA |
| Sequence Analysis | Mutation Surveyor v3.20 | SoftGenetics | State College, PA, USA |

Example 4

In Vitro Selection of Influenza Variants

A Biomek FX liquid handler (Beckman Coulter, Brea, Calif., USA) was used to plate MDCK cells ($4\times10^5$ cells/mL) into black, clear bottom, 384-well plates at a density of $2\times10^4$ cells per well in 50 µL of viral growth media (VGM: Dulbecco's modified eagle medium (DMEM) supplemented with penicillin/streptomycin, L-glutamine, HEPES and 1 µg/mL TPCK-treated trypsin). Cells were incubated 5 h at 37° C., 5% $CO_2$, with humidity to allow cells to adhere and form a monolayer. Using a Biomek FX, 40 µL of media was removed, and replaced with 25 µL of VGM containing diluted drug (final DMSO concentration of 0.5% DMSO) and 15 µL of virus at an MOI of 1 (20,000 $TCID_{50}$/well), for a total of 50 µL. Drug was added to 32 replicate wells at each of eight concentrations of Compound 1, ranging from 1× to 128× the $EC_{50}$. Internal controls consisted of 64 wells containing cells only and 64 wells with virus infected cells in the absence of compound. Plates were incubated at 37° C., 5% $CO_2$, with saturating humidity, for 72 h. After incubation, 20 µL of supernatant was harvested and diluted in 150 µL of cDMEM. 20 µL CellTiter-Glo was added to the plate containing 30 µL of media and cells using a Biomek FX and incubated at room temperature for 10 min. Luminescence, which is a measure of cell viability via total ATP in cells, was measured using an EnVision plate reader (PerkinElmer, Waltham, Me., USA) to monitor the effect of virus grown in the presence of compound. Diluted supernatant virus was passaged to new wells. Two additional virus passages were performed. After a total of three passages, wells showing virus growth in the presence of inhibitor were expanded to small virus stocks, and these stocks were characterized for Compound 1 sensitivity in a 3 day MDCK cell protection assay. For stocks showing reduced sensitivity to Compound 1, the PB1, PB2, and PA coding sequences were determined following RNA isolation, reverse transcription PCR, PCR amplification and Sanger-based population sequencing. To identify potential Compound 1 resistant variants for testing in the reverse genetics-based system, several criteria were used. The virus needed to demonstrate an $EC_{50}$ shift in Compound 1 sensitivity of greater than 10-fold (to be outside the assay-to-assay variation of 3- to 5-fold) and be observed in multiple experimental wells. Additionally, any variants at PB2 positions previously identified to confer resistance to Compound 1 were also analyzed. Lastly to remove common polymorphisms not related to Compound 1, the variant was excluded if observed in control wells. Amino acid changes from the parent strain were identified and cloned into the A/Puerto Rico/8/34 influenza background using a 12-plamid reverse genetics system. The phenotype of the reverse genetics influenza strains was again characterized by the 3 day MDCK cell protection, inhibitor sensitivity assay. The natural frequency of the identified variants was analyzed by searching public databases of influenza sequences and the location of the identified amino acid changes within the available PB2 X-ray crystal structure was evaluated.

To allow productive infections in a canine kidney cell line (MDCK), A/Wisconsin/67/2005 was serially passaged 10 times in MDCK cells. This adapted virus was plaque purified and plaque #1 was designated as A/Wisconsin/67/2005-p1. Sequence comparison between the parental and plaque #1 A/Wisconsin/67/2005 viruses show that the PA, PB1 and PB2 sequences are identical. Sensitivity to Compound 1 in a 3 day MDCK cell-based CPE assay with A/Wisconsin/67/2005-p1 was determined to be 0.0020 µM.

Selection of A/Wisconsin/67/2005-p1 (herein referred to as A/Wisconsin/67/2005) variants with reduced susceptibility to Compound 1 was performed. Selections were carried out at Compound 1 concentrations ranging from the $EC_{50}$ to 128×-$EC_{50}$ (i.e., 0.0020 µM-0.256 µM). Following three passages at the same concentration per well, enriched viral populations were harvested from the supernatant. Sixteen potential Compound 1-resistant variant containing wells (i.e., those with <50% of ATP levels compared to uninfected wells) and 16 control wells were selected for confirmatory phenotypic analysis and sequencing of polymerase genes (Tables 3 and 4).

TABLE 3

A/Wisconsin/67/2005 Variants Selected With Compound 1

| EC50 Shift | Sample Number | Variant Summary | PB2 | | | | | | | | | | | | PA | |
|---|---|---|---|---|---|---|---|---|---|---|---|---|---|---|---|---|
| | | | M11 | Q306 | F323 | S324 | K339 | F363 | K376 | I411 | M431 | D506 | N510 | M535 | V463 | I505 |
| 733 | 6 | S324R | | | | R | | | | | | | | | | |
| 533 | 1 | S324N | | | | N | | | | | | | | | | |
| 440 | 5 | M11M/T, K376N | M/T | | | | | | N | | | | | | | |
| 353 | 8 | N510K | | | | | | | | | | | K | | | |
| 347 | 2 | K376N | | | | | | | N | | | | | | | |
| 227 | 3 | I411V, N510K | | | | | | | | V | | | K | | | |
| 113 | 7 | F323S | | | S | | | | | | | | | | | |
| 59 | 10 | Q306L | | L | | | | | | | | | | | | |
| 41 | 4 | M431I | | | | | | | | | I | | | | | |
| 9 | 9 | I411V, D506G | | | | | | | | V | | G | | | | |
| 5 | 11 | F363L | | | | | | L | | | | | | | | |
| 3 | 14 | | | | | | | | | | | | | | | |
| 1 | 12 | PA V463I, PA I505L | | | | | | | | | | | | | I | L |
| 1 | 13 | M535V | | | | | | | | | | | | V | | |
| 1 | 15 | S324S/C, K339K/I | | | | S/C | K/I | | | | | | | | | |
| 1 | 16 | | | | | | | | | | | | | | | |

TABLE 4

A/Wisconsin/67/2005/Control Variants, Selected Without Compound 1

| EC50 Shift | Sample Number | Variant Summary | PB2 | | | PB1 |
|---|---|---|---|---|---|---|
| | | | T35 | I411 | I726 | P5 |
| 1 | 17 | | | | | |
| 1 | 18 | | | | | |
| 1 | 19 | | | | | |
| 1 | 20 | I411I/V | | I/V | | |
| 1 | 21 | I411I/V | | I/V | | |
| 1 | 22 | | | | | |
| 1 | 23 | T35I | I | | | |
| 1 | 24 | PB1 P5P/L | | | | P/L |
| 1 | 25 | | | | | |
| 1 | 26 | | | | | |
| 1 | 27 | | | | | |
| 1 | 28 | I726I/V, PB1 P5P/L | | | I/V | P/L |
| 1 | 29 | | | | | |
| 1 | 30 | | | | | |
| 1 | 31 | | | | | |
| 1 | 32 | | | | | |

TABLE 5

Summary of Compound 1 Resistant Variants

| PB2 Variant | Strain(s) Observed[a] | Number Observed[b] | Compound 1 Fold EC50 Shift of Reverse Genetics Virus, Mean[c] | Percent of Peak In Vitro Titer[d] | Frequency in Human Dataset[e] |
|---|---|---|---|---|---|
| Q306H | PR | 2 | 154 | 6% | 0/8919 |
| Q306L | WI | 1 | ND[f] | ND[f] | 0/8919 |
| F323S | WI | 1 | 111 | 1% | 3/8942 |
| F323Y | PR | 1 | 100 | ND[f] | 0/8942 |
| S324G | PR | 1 | 18 | 38% | 0/8942 |
| S324I | PR | 1 | 184 | 6% | 0/8942 |
| S324N | PR, WI | 3 | 84 | 18% | 1/8942 |
| S324R | PR, WI | 20 | 57 | 18% | 0/8942 |
| S337L | CA | 1 | 22 | 6% | 0/8944 |
| S337P | CA | 1 | 4.9 | 1% | 2/8944 |
| F363L | CA, WI | 4 | 26 | 8% | 1/8911 |
| K376N | WI | 2 | ND[f] | ND[f] | 0/8910 |
| K376Q | CA | 1 | 262 | ND[g] | 0/8910 |
| K376R | PR, CA | 8 | 100 | 10% | 0/8910 |
| F404Y | PR | 5 | 378 | 56% | 3/8912 |
| M431I | WI | 1 | 57 | 8% | 0/8914 |
| M431T | PR | 2 | 116 | 1% | 0/8914 |
| N510K | WI | 2 | 514 | 1% | 0/8926 |
| N510T | PR | 3 | 205 | 32% | 1/8926 |

Note:
Several variants that were observed once were chosen for phenotypic analysis via reverse genetics because variants at these amino acid positions were observed in prior resistance selection experiments.
[a]Passage strain variant was observed in: CA, A/California/07/2009; PR, A/Puerto Rico/8/34; WI, A/Wisconsin/67/2005
[b]The number of wells in which the specific variant was observed
[c]Reverse genetics viruses with alterations only at the indicated position were constructed and tested for Compound 1 sensitivity in a 3 day CPE-based assay. Fold-shifts are defined by dividing mutant EC50 by wild type virus. Compound 1 fold EC50 shifts are averages of at least three independent experiments.
[d]MDCK cells were infected with the indicated virus at an MOI = 0.01 and supernatants were titered over 62 hours. Percent of peak titer was determined as a percentage of variant mean antilog titer divided by wild-type mean antilog titer at 48 hours post infection. Virus replication capacity was assayed in one experiment with triplicate repeats.
[e]Summary of all publicly available human influenza A sequences (pan subtype) included in the Vertex Flu Research database on Mar. 20, 2013
[f]ND Not determined
[g]ND Not determined because titer was below the limit of detection at 48 hours Of the 16 Compound 1 passaged virus isolates, 9 had a confirmed >10-fold EC50 shift. These 9 viruses all contained PB2 variants at positions previously characterized as conferring resistance to Compound 1 in A/Puerto Rico/8/34 and/or A/California/07/2009 (emboldened text in Table 3; Table 5). The >200-fold Compound 1-resistant viruses contained PB2 variants S324R, S324N, K376N or N510K, while F323S, Q306L, and M431I were observed in the less resistant viruses (10-200 fold). The F363L variant was observed in a virus conferring 5-fold resistance. Novel variants observed in this study were at previously characterized PB2 positions were Q306L, K376N, M431I and N510K. No PA or PB1 variants were associated with Compound 1 resistance in this study. While no PB1 variants were observed from the Compound 1 passaged wells, 2 PA variants were observed in wells that did not have a confirmed decrease in sensitivity to Compound 1 (1×$EC_{50}$).

Characterization of individual potential Compound 1-resistant variants using reverse genetics methods is underway. To date, these viruses have demonstrated Compound 1 $EC_{50}$ shifts ranging from 4.9- to 514-fold (Table 5). Since all the variants were generated using an A/Puerto Rico/8/34 reverse genetics system, which contains sequences conferring M2-inhibitor resistance and NAI sensitivity, cross-resistance studies were not performed.

To assess the replication capacity of the viruses identified in resistance selection studies, MDCK cells were infected with reverse genetics generated variants at a very low MOI (0.01) and viral titers were monitored over a 62 hour period. Peak titer for wild-type virus was determined to be at 48 hours post infection, so all mutant viruses were compared at this time point. In all cases, the PB2 mutant viruses were unable to grow to equivalent titers as wild-type virus (Table 5). Only F404Y achieved a titer greater than half that of wild-type (56%). 10 viruses showed titers no more than 10% of that of wild-type: Q306H, F323S, S324I, S337L, S337P, F363L, K376R, M431I, M431T and N510K. K376Q was assayed and at 48 hours post-infection, viral titers were lower than the limit of detection. Of note, this assay was performed one time, with each virus being represented at least 3 times in that assay. The three values for each virus, at each time point were averaged.

Example 5

Characterization of Sensitivity of Influenza Variants to Compound 1

Compound antiviral activity was evaluated by its ability to prevent MDCK cell death as a consequence of influenza virus infection, as measured by cellular ATP levels using CellTiter-Glo. Briefly, a Biomek FX liquid handler was used to plate MDCK cells (4×10⁵ cells/mL) into black, clear bottom, 384-well plates at a density of 2×10⁴ cells per well in 50 μL VGM. Cells were incubated for 5 h at 37° C., 5% $CO_2$, with saturated humidity to allow cells to adhere and form a monolayer. Using a Biomek FX, 40 μL of media was removed, 25 μL of VGM containing diluted drug (final DMSO concentration of 0.5% DMSO), and 15 μL of virus at a concentration of 100 $TCID_{50}$/well was added. Internal controls consisted of wells containing cells only and cells infected with virus in the absence of compound. Plates were incubated at 37° C., 5% $CO_2$, and saturating humidity for 72 h. After incubation, 20 μL of CellTiter-Glo was added to each well using a Biomek FX and incubated at room temperature for 10 min. Luminescence was measured using an EnVision plate reader (PerkinElmer). $EC_{50}$ (compound concentration at which CPE is half that of control) values were calculated by fitting the compound dose versus response data using a 4-parameter curve fitting method of Levenburg Marquardt algorithm (Condoseo software; Genedata Basel, Switzerland).

Example 6

Determination of Viral Replication Competency

Viral replication competency was assayed for reverse genetics variants via 62-hour growth curves in infected MDCK cells. MDCK cells were plated in 96-well plates at a density of 4×10⁴ cells per well and infected with virus at an MOI=0.01 in the absence of compound. At various time points plates were harvested and supernatant was assayed for virus titer. Virus titers were plotted over time and peak titer for wild-type virus was determined to occur at 48 hours post infection.

Example 7

Amplification and Sequencing of the Influenza A Polymerase Complex from Viral Stocks or Infected MDCK Cells Sequence analysis of influenza A virus utilized a reverse-transcriptase polymerase chain reaction (RT-PCR) amplification of an approximately 2.5 kilobase RNA fragments for the PB2, PB1, and PA coding regions. Viral RNA was extracted from 100 μL of viral stock or from 2×10⁶ infected MDCK cells in 300 μL of lysis buffer under denaturing conditions. Viral RNA was isolated by standard commercial silica-gel membrane using either the RNeasy Plus Mini method (catalog number 74134, Qiagen, Valencia, Calif., USA) or the QIAamp Virus RNA Mini method (catalog number 52904, Qiagen). A complementary DNA (cDNA) fragment was synthesized from viral RNA in a 50 μL reaction containing 2.5 μM of a Universal 12 primer (AGCRAAAGCAGG) (SEQ ID NO: 2), 400 U of Superscript™ III Reverse Transcriptase (catalog number 18080-044, Invitrogen, Carlsbad, Calif.), 40 U of RNase OUT (catalog number 10777-019, Invitrogen), PC2 reaction buffer (50 mM Tris-HCl pH 9.1, 16 mM ammonium sulfate, 3.5 mM magnesium chloride, and 150 μg/mL bovine serum albumin) (catalog number 1001, AB Peptides, St. Louis, Mo., USA), 500 μM dNTPs (catalog number 639125, Clontech, Mountain View, Calif., USA), and 5 mM dithiolthreitol (catalog number 18080-044, Invitrogen), with a denaturation step (65° C. for 5 min) followed by ramping extension temperatures (25° C. for 10 min, 42° C. for 10 min, 50° C. for 20 min, 55° C. for 10 min, and 70° C. for 15 min) in the RT reaction. To amplify influenza A virus polymerase subunit-encoding fragments from the synthesized cDNA pool, 5 μL of the completed RT reaction was combined with PC2 reaction buffer, 200 μM dNTPs (catalog number 639125, Clontech), 1.5 M betaine (catalog number, B0300, Sigma Aldrich,), 3.2 U Klentaq DNA polymerase (catalog number 1001, AB Peptides), 1.6 U Pfu DNA polymerase (catalog number 600160, Stratagene, La Jolla, Calif., USA), and 400 μM each primer for a final reaction volume of 50 μL (for PA segment: Forward: 5'-CGTCTCNGGGAGCGAAAGCAG-GTACTGATCCAAAAT (SEQ ID NO: 3) and Reverse: 5'-CGTCTCNTATTAGTAGAAACAAGGTACTTTT-TTGGA (SEQ ID NO: 4), for PB1 segment: Forward: 5'-CGTCTCNGGGAGCGAAAGCAGGCAAACCATTT-GAA (SEQ ID NO: 5) and Reverse: 5'-CGTCTCNTATT-AGTAGGAACAAGGCATTTTTTCATG (SEQ ID NO: 6), for PB2 segment: Forward: 5'-CGTCTCNGGGAGC-GAAAGCAGGTCAATTATATTCAA (SEQ ID NO: 7) and Reverse: 5'-CGTCTCNTATTAGTAGAAACAAGGTC-GTTTTTAAAC (SEQ ID NO: 8)). The reaction was incubated at 94° C. for 2 min, followed by 40 cycles at 94° C. for 15 s, 68° C. −0.4° C./cycle ('touchdown' PCR) for 20 s, and 68° C. for 3.5 min, followed by incubation at 68° C. for 7 min. The PCR product was purified using the QIAquick 96 PCR Purification kit (catalog number 28181, Qiagen) and an aliquot was analyzed by 1% agaraose gel electrophoresis for quality. The purity and quantity of the purified PCR products were evaluated using spectrophotometry (NanoDrop, 8000 v.1.1; Thermo Fisher Scientific). Purified DNA was sequenced in-house or sent to Beckman-Coulter (Agencourt® Biosciences; Danvers, Mass., USA) for sequencing of the PB2, PB1 and PA segments.

Sequence traces were aligned and interpreted using Mutation Surveyor software (SoftGenetics, State College, Pa.). Amino acid substitutions were detected by comparing sequences to the corresponding virus used for resistance selection (i.e., A/Wisconsin/67/2005).

Example 8

Construction of Plasmids for Reverse Genetics

Plasmid constructs encoding viral genome segments were created as follows. Influenza A/Puerto Rico/8/34 virus RNA isolation and cDNA synthesis were performed. cDNA was amplified using oligos containing terminal BsmB1 restriction endonuclease sites, and the amplified product was cloned into the pCR-XL-TOPO shuttle vector using a TOPO® XL PCR Cloning Kit (catalog number K4700-10, Invitrogen). The cDNA-containing TOPO vectors were digested with BsmB1 and inserts ligated into the RNA polymerase I-driven expression vector pHH21. Plasmids were sequenced to confirm proper integration of the cDNA fragment and the absence of unwanted mutations.

Amino acid changes from the parent strain, identified from resistance selection experiments, were cloned into the corresponding pHH21-A/Puerto Rico/8/34 plasmid using the Quick Change™ II XL Site-Directed Mutagenesis Kit (catalog number 200518, Agilent Technologies, Inc., Wilmington, Del., USA) following the manufacturer's protocol. Briefly, 10 ng of wild-type plasmid and 150 ng of each forward and reverse mutation-containing primer were combined with 5 μL 10× reaction buffer, 1 μL dNTP mix, 3 μL QuikSolution and 2.5 U of PfuUltra HF DNA polymerase in PCR grade water to 50 μL, and mutations were introduced by PCR. Thermal cycling was performed with an initial denaturation at 95° C. for 1 min, 18 cycles of 95° C. for 50 s, 60° C. for 50 s, and 68° C. for 5 min and a final extension for 7 min at 68° C. Residual wild-type plasmid was digested with Dpn I restriction enzyme, and mutation-containing plasmid was transformed into *E. coli*, overnight colony screening and plasmid was isolated using a QIAGEN Plasmid Plus midi kit (catalog number 12943, Qiagen). Proper incorporation of point mutations into the plasmid was confirmed by sequencing.

Example 9

Generation of Recombinant Viruses

To investigate mutations, recombinant viruses were generated by transient transfection of 293T cells (HEK 293T/17, CRL-11268, ATCC) with a plasmid mixture containing 1.25 μg of the pHH21 mutation-containing plasmid, each of the seven remaining pHH21 wild-type plasmids, and the four RNP complex expression plasmids. Transient transfections were performed with TransIT-LT1 transfection reagent (catalog number MIR 2300, MirusBio, Madison, Wis., USA). Briefly, a 1:2 mixture (w/v) of the plasmid mixture and transfection reagent was incubated in 1.5 mL of OPTI-MEM I media (catalog number 11058, Invitrogen) at room temperature for 15 min. The transfection mixture was then added to T-75 flasks containing 293T cells at 50% confluency in 15 mL OPTI-MEM I media (293T cells maintained in 15 mL cDMEM supplemented 10% FBS which were washed twice with OPTI-MEM I media before addition of transfection mixture). Cells were incubated at 37° C. in 5% $CO_2$ at saturated humidity for 72 h. Following incubation, the supernatant was harvested and centrifuged at 650×g for 10 min to remove cell debris and virus was further expanded in MDCK cells infected at low MOI after which viral stocks were harvested and titered.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages and modifications are within the scope of the following claims.

What is claimed is:

1. An isolated influenza A virus polynucleotide, or a biologically active fragment thereof, said polynucleotide comprising a nucleotide sequence which encodes an influenza A virus polymerase, wherein the polymerase comprises an amino acid sequence of SEQ ID NO: 1 with at least one amino acid substitution selected from the group consisting of amino acid 306, 323, 324, 337, 376, and 431.

2. The isolated influenza A virus polynucleotide of claim 1, wherein the polynucleotide encodes an influenza A virus polymerase with a mutation at amino acid position 306, wherein said mutation encodes an amino acid other than the amino acid Q, or encodes the amino acid H, or L.

3. The isolated influenza A virus polynucleotide of claim 1, wherein the polynucleotide encodes an influenza A virus polymerase with a mutation at amino acid position 323, wherein said mutation encodes an amino acid other than the amino acid F, or encodes the amino acid S, or Y.

4. The isolated influenza A virus polynucleotide of claim 1, wherein the polynucleotide encodes an influenza A virus polymerase with a mutation at amino acid position 324, wherein said mutation encodes an amino acid other than the amino acid S, or encodes the amino acid G, or I, or N, or R.

5. The isolated influenza A virus polynucleotide of claim 1, wherein the polynucleotide encodes an influenza A virus polymerase with a mutation at amino acid position 337, wherein said mutation encodes an amino acid other than the amino acid S, or encodes the amino acid L, or P.

6. The isolated influenza A virus polynucleotide of claim 1, wherein the polynucleotide encodes an influenza A virus polymerase with a mutation at amino acid position 376, wherein said mutation encodes an amino acid other than the amino acid K, or encodes the amino acid N, or Q, or R.

7. The isolated influenza A virus polynucleotide of claim 1, wherein the polynucleotide encodes an influenza A virus polymerase with a mutation at amino acid position 431, wherein said mutation encodes an amino acid other than the amino acid M, or encodes the amino acid I, or T.

8. The isolated influenza A virus polynucleotide of claim 1, wherein said polynucleotide encodes two or three amino acid substitutions at amino acid positions selected from the group consisting of amino acids 306, 323, 324, 337, 376, and 431 relative to a wild-type influenza A virus polymerase.

9. An isolated influenza A virus polymerase comprising an amino acid sequence of SEQ ID NO: 1, in which the amino acid sequence of SEQ ID NO: 1 has at least one amino acid substitution at an amino acid position selected from the group consisting of 306, 323, 324, 337, 376, and 431 which said amino acid substitution is different from the amino acid at the corresponding position of the wild-type influenza A virus polymerase comprising an amino acid sequence of SEQ ID NO: 1.

10. An expression system comprising the influenza A virus polynucleotide of claim 1.

11. The expression system of claim 10 comprising a vector, wherein the vector comprises the influenza A virus polynucleotide of claim 1 operably linked to a promoter.

12. A host cell transfected, transformed, or transduced with the vector of claim 11.

13. The expression system of claim 10 that is an mRNA display system.

14. An isolated influenza A virus variant comprising a polynucleotide encoding an influenza A virus polymerase of SEQ ID NO: 1, wherein at least one amino acid corresponding to at least one amino acid position selected from the group consisting of 306, 323, 324, 337, 376, and 431 of said influenza A virus polymerase is mutated such that it encodes an amino acid different from the corresponding amino acid of the wildtype influenza A virus polynucleotide having an amino acid sequence of SEQ ID NO: 1.

* * * * *